United States Patent
Daum et al.

(10) Patent No.: US 10,401,291 B2
(45) Date of Patent: *Sep. 3, 2019

(54) STANDING WAVE INTERFEROMETRIC MICROSCOPE

(71) Applicant: FEI Company, Hillsboro, OR (US)

(72) Inventors: Rainer Daum, Wessling (DE); Xaver Voegele, Munich (DE)

(73) Assignee: FEI COMPANY, Hillsboro, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 15/880,945

(22) Filed: Jan. 26, 2018

(65) Prior Publication Data

US 2018/0195962 A1 Jul. 12, 2018

Related U.S. Application Data

(63) Continuation of application No. 15/246,512, filed on Aug. 24, 2016, now Pat. No. 9,885,660.

(30) Foreign Application Priority Data

Oct. 21, 2015 (EP) .................................... 15190749

(51) Int. Cl.
*G01N 21/64* (2006.01)
*G02B 21/14* (2006.01)
(Continued)

(52) U.S. Cl.
CPC ......... *G01N 21/6458* (2013.01); *G01N 21/45* (2013.01); *G02B 21/06* (2013.01);
(Continued)

(58) Field of Classification Search
CPC .... G01N 21/45; G01N 21/6458; G02B 21/06; G02B 21/16
See application file for complete search history.

(56) References Cited

U.S. PATENT DOCUMENTS

RE38,307 E 11/2003 Gustafsson et al.
7,463,344 B2 12/2008 Wolleschensky et al.
(Continued)

FOREIGN PATENT DOCUMENTS

EP 0491289 B1 4/1996

OTHER PUBLICATIONS

"Fluorophore", Wikipedia, Retrieved from the Internet Nov. 7, 2016, https://en.wikipedia.org/wiki/Fluorophore, 10 pages.
(Continued)

*Primary Examiner* — Marcus H Taningco (57) ABSTRACT

A standing wave interferometric microscope is disclosed herein. An example microscope may include an illuminator, for illuminating a specimen with a standing wave of input radiation at an analysis location to cause the specimen to fluoresce, the specimen arranged in the analysis location, a pair of projection systems, arranged at opposite sides of the analysis location, coupled to collect at least a portion of the fluorescence and direct a corresponding pair of fluorescence light beams into a respective pair of inputs of an optical combining element, a wavefront modifier for producing astigmatism in at least one of the fluorescence light beams entering the optical combining element, and a detector for examining output light from said combining element.

20 Claims, 6 Drawing Sheets

(51) Int. Cl.
| | |
|---|---|
| *G02B 21/16* | (2006.01) |
| *G02B 27/58* | (2006.01) |
| *G01N 21/45* | (2006.01) |
| *G02B 21/06* | (2006.01) |
| *G02B 21/08* | (2006.01) |
| *G02B 21/18* | (2006.01) |
| *G02B 21/36* | (2006.01) |
| *G02B 21/00* | (2006.01) |

(52) U.S. Cl.
CPC .......... *G02B 21/088* (2013.01); *G02B 21/14* (2013.01); *G02B 21/16* (2013.01); *G02B 21/18* (2013.01); *G02B 21/361* (2013.01); *G02B 21/364* (2013.01); *G02B 27/58* (2013.01); *G02B 21/008* (2013.01); *G02B 21/0056* (2013.01)

(56) References Cited

U.S. PATENT DOCUMENTS

| | | | |
|---|---|---|---|
| 7,583,436 | B2 | 9/2009 | Rygiel |
| 7,599,069 | B2 | 10/2009 | Toussaint et al. |
| 7,924,432 | B2 | 4/2011 | Hess et al. |
| 8,237,835 | B1 | 8/2012 | Muller |
| 9,885,660 | B2 * | 2/2018 | Daum ................ G02B 21/361 |
| 2005/0006597 | A1 | 1/2005 | Wolleschensky et al. |
| 2006/0098188 | A1 | 5/2006 | Buijsse et al. |
| 2006/0291043 | A1 | 12/2006 | Bewersdorf et al. |
| 2008/0007248 | A1 | 1/2008 | Zyss et al. |
| 2008/0158551 | A1 | 7/2008 | Hess |
| 2009/0263002 | A1 | 10/2009 | Cremer et al. |
| 2012/0002031 | A1 | 1/2012 | Pertsinidis et al. |
| 2012/0193530 | A1 | 8/2012 | Parker et al. |
| 2014/0160265 | A1 | 6/2014 | Voegele et al. |
| 2014/0231644 | A1 | 8/2014 | Botman et al. |
| 2014/0293015 | A1 | 10/2014 | Hess |
| 2014/0333750 | A1 * | 11/2014 | Zhuang ................ G02B 21/367 348/79 |
| 2015/0002632 | A1 * | 1/2015 | Kalkbrenner ...... G01N 21/6458 348/46 |
| 2015/0014552 | A1 * | 1/2015 | Nagatomi ............ G01N 21/645 250/458.1 |
| 2015/0028205 | A1 | 1/2015 | Botman et al. |
| 2016/0003740 | A1 * | 1/2016 | Tao ........................ G01N 21/45 250/459.1 |

OTHER PUBLICATIONS

"Super Resolution Microscopy", Wikipedia, Retrieved from the Internet Nov. 4, 2016, https://en.wikipedia.org/wiki/Super-resolution_microscopy, 15 pages.

Aquino, Daniel et al., "Two-color nanoscopy of three-dimensional vols. By 4Pi detection of stochastically switched fluorophores". Nature Methods, vol. 8. No. 4., Apr. 1, 2011. pp. 353-359. XP055260855. GB ISSN: 1548-7091. DOI: 10.1038/nmeth.1583.

Hell, Stefan W. et al., "Enhancing the Axial Resolution in Far-field Light Microscopy: Two-photon 4Pi Confocal Fluorescence Microscopy," J.Modern Optics (1994), vol. 41 No. 4) pp. 675-681.

Lippincott-Schwartz, J., et al. "Photoactivatable fluorescent proteins for diffraction limited and super-resolution imaging", Trends Cell Biology, Nov. 2009, pp. 555-565, vol. 19 Issue 11, Elsevier.

Raymo, F. "Photoactivatable Fluorophores", ISRN Physical Chemistry, Aug. 16, 2012, vol. 2012, Article ID 619251, 16 pages.

Shao, L., et al. "I5S: Wide-Field Light Microscopy with 100-nm-Scale Resolution in Three Dimensions", Biophysical Journal, Jan. 6, 2009, pp. 4971-4983, vol. 94 Issue 12.

Shtengel, G., et al. "Interferometric fluorescent super-resolution microscopy resolves 3D cellular ultrastructure", PNAS, Feb. 6, 2009, pp. 3125-3130, vol. 106 No. 09.

Unknown, "Super Resolution Microscopy," Retrieved from the Internet Nov. 7, 2016; http://www.mechanobio.info/topics/methods/super-resolution-microscopy-intro; 11 pages.

* cited by examiner

STANDING WAVE INTERFEROMETRIC MICROSCOPE

PRIORITY INFORMATION

This application is a continuation of U.S. application Ser. No. 15/246,512, filed Aug. 24, 2016, issued as U.S. Pat. No. 9,885,660 on Feb. 6, 2018, and claims priority to European application number 15190749.0, filed Oct. 21, 2015, which is incorporated herein for all purposes.

FIELD OF THE INVENTION

The invention relates in general to microscopy, and specifically to wide-field interferometric microsopy.

BACKGROUND OF THE INVENTION

The interferometric Photo-Activated Localization Microscopy (iPALM) technique can be regarded as a refinement of the conventional (non-interferometric) PALM technique, whereby the former augments the latter with the ability to perform resolution/image reconstruction axially as well as laterally. The augmentation can be understood in several ways, as discussed below.

In PALM, lateral super-resolution is achieved by sequentially exciting spatially sparse subsets of objects (photoactivatable fluorophores) in a specimen, causing temporal separation of fluorescence emission from these different subsets. The resolvability of objects within each of these sparse subsets is greater than if the whole specimen were to be imaged in one go. In essence, the resolution-limiting diffraction effects that one would expect if one were to attempt to simultaneously image a dense set of objects are circumvented by instead regarding the set as a cumulative collective of sparse subsets, which are sequentially imaged. The photoactivatable fluorophores are caused to fluoresce in a two-step process, whereby in a preliminary step, a so-called "activating wavelength" (or "activation wavelength") is used to promote the fluorophore from a non-emissive to an emissive state; and in a subsequent step, a so-called "exciting wavelength" (or "excitation wavelength") is used to cause radiative "relaxation" of the activated fluorophore (fluorescence excitation).

In iPALM, the lateral (XY) super-resolution achieved in PALM is taken a step further, by introducing a mechanism that will also allow fine axial/depth (Z) resolution. This is achieved by imaging the (fluorophores in the) specimen through a pair of oppositely disposed projection systems (objective lenses, optical columns), whose output beams are fed into an optical combining element (specifically, a three-phase beam splitter), where they optically interfere. The resulting interference fringe pattern will be (very) sensitive to the axial (depth) position of the object (fluorophore) being imaged, since this will influence the relative path lengths of the interfering beams. By using a detector arrangement comprising multiple detectors (e.g. CCDs) to selectively look at phase-separated outputs from the combining element, one can effectively (mathematically) "translate" a given fringe pattern into a deduced axial object position; in iPALM, three distinct outputs from the combining element (mutually phase-shifted by 120°) are observed using three different detectors (cameras), whereby the relative intensities of the outputs observed by these cameras will change in a predictable manner as a function of axial fluorophore position.

Although iPALM is a useful technique, it does suffer from drawbacks. More specifically, it relies on a relatively complicated optical/detection architecture. In particular the employed three-phase beam splitter is an expensive and fragile component that is difficult to manufacture. Its performance is sensitive to temperature fluctuations and mechanical vibrations, and it has a relatively long settling time after being disturbed. Moreover, it is difficult to optically align/adjust. The employed three-phase beam splitter is also difficult to mechanically scale up in size, e.g. to match cameras with a larger field of view (without vignetting). Limiting factors in this regard include tolerances on the planar optics of the beam splitter, and coherence characteristics of the fluorescence light. The detection set-up requires the use of three detectors/cameras, which increases bulk/decreases available space, and increases expense.

One should note the distinction between a wide-field microscope—which can be regarded as employing a planar imaging wave—and, for example, a point scanning microscope (German: "Rastermikroscop"), which uses an imaging beam that is focused to a point, and is thus (necessarily) scanned over an object to be imaged. The present invention relates to the former (wide field).

It is an object of the invention to address these issues. In particular, it is an object of the invention to provide an alternative depth-resolved localization microscopy technique that utilizes a radically different illumination/detection configuration. More specifically, it is an object of the invention that does not require use of a three-phase beam splitter.

BRIEF DESCRIPTION OF THE DRAWINGS

Like reference numerals refer to corresponding parts throughout the several views of the drawings.

DETAILED DESCRIPTION OF EMBODIMENTS

The above described deficiencies may be addressed by a microscope as disclosed herein. In some embodiments, an illuminator comprises an optical cavity that is configured to produce a standing wave of input radiation at an analysis location, and a detector arrangement includes two interferometric detection branches.

To illustrate, (i) the standing wave alluded to here may be produced using the "activating" input light or the "exciting" input light, and will extend in a direction along the (local) optical axis at the analysis location, and (ii) this standing wave produces a (sinusoidal) modulation of the input radiation that illuminates the specimen, and it has a phase that can be tuned, e.g. by adjusting the "length" of the optical cavity in which it is generated. Further, aspect (ii) can be exploited to provide an alternative for (at least) one of the three 120-degree-phase-shifted beams used in the conventional iPALM detection set-up. For example, since three detection beams are thus rendered unnecessary, one no longer needs to use a troublesome three-phase beam splitter and associated trio of cameras—instead, one can suffice with a regular two-way beam splitter, which is much cheaper, less fragile, and more easily manufactured (and scaled to larger sizes). Moreover, (iv) the spatially modulated intensity distribution in the standing wave admits innovative ways of activating/exciting the fluorophores in the specimen, which can serve as a basis for new effects and advantages.

Note that the invention is distinguished from detector arrangements that use only one detector (branch/channel), e.g. as set forth in US 2005/0006597 A1 and EP 0 491 289 A1. In such set-ups, although one can observe an interferometric image, one cannot meaningfully interpret detected intensities; for example, one does not know if an above-average intensity value is due to constructive interference effects, or instead due to a fluorophore with a relatively high emission rate, or to a combination of both. Using more than one channel allows examination of intensity ratios, thus mitigating this problem. And further distinguished from detector arrangements that use three detectors (branches/channels), e.g. as described above/below, and as set forth in US 2006/0291043 A1 (in which it should be noted that no interferometric imaging is done: the three employed cameras are only used to detect different wavelengths).

Figure 1:
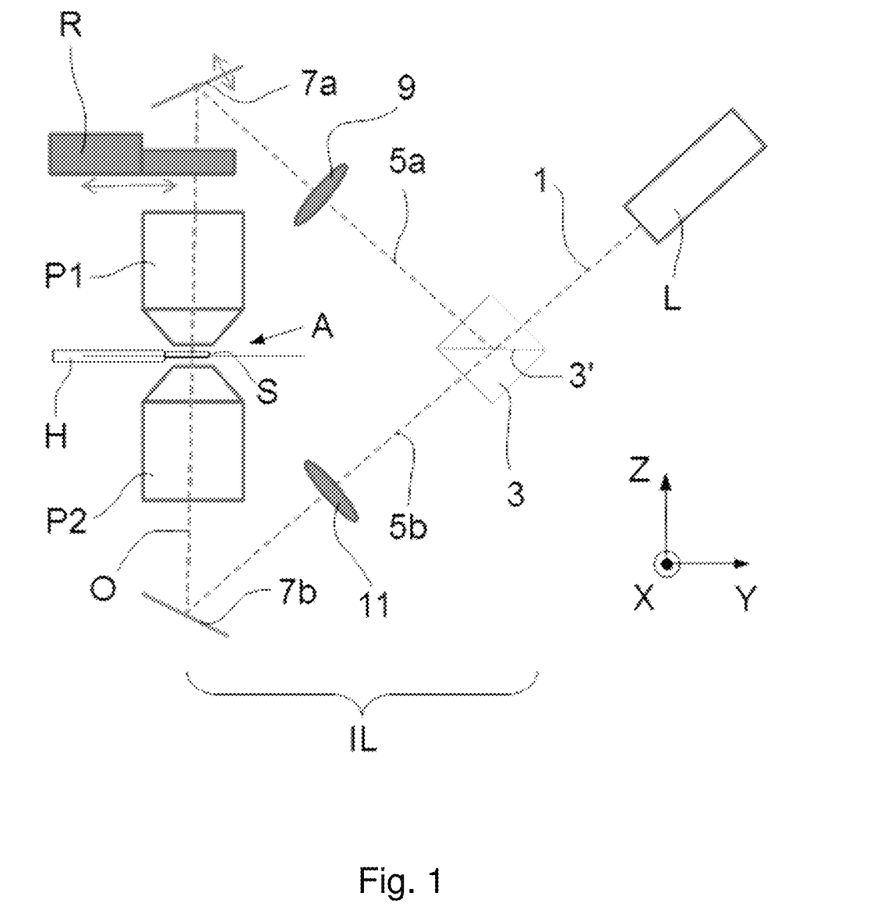
FIG. 1 illustrates a longitudinal cross-sectional view of part of an embodiment of a microscope according to the present invention.

There are various ways in which to realize/configure an illuminator of the type disclosed herein. In an embodiment, the illuminator comprises a beam splitter to produce a pair of coherent beams from a single source (e.g. a laser), a pair of reflectors to direct each of said pair of coherent beams through a respective one of the employed pair of projection systems, where the optical cavity comprises the beam splitter and the pair of reflectors. An example of such a set-up is depicted in FIG. 1. Such a configuration can be regarded as a "dual-insertion" architecture because the standing wave is generated using two oppositely-directed input beams.

Figure 2:
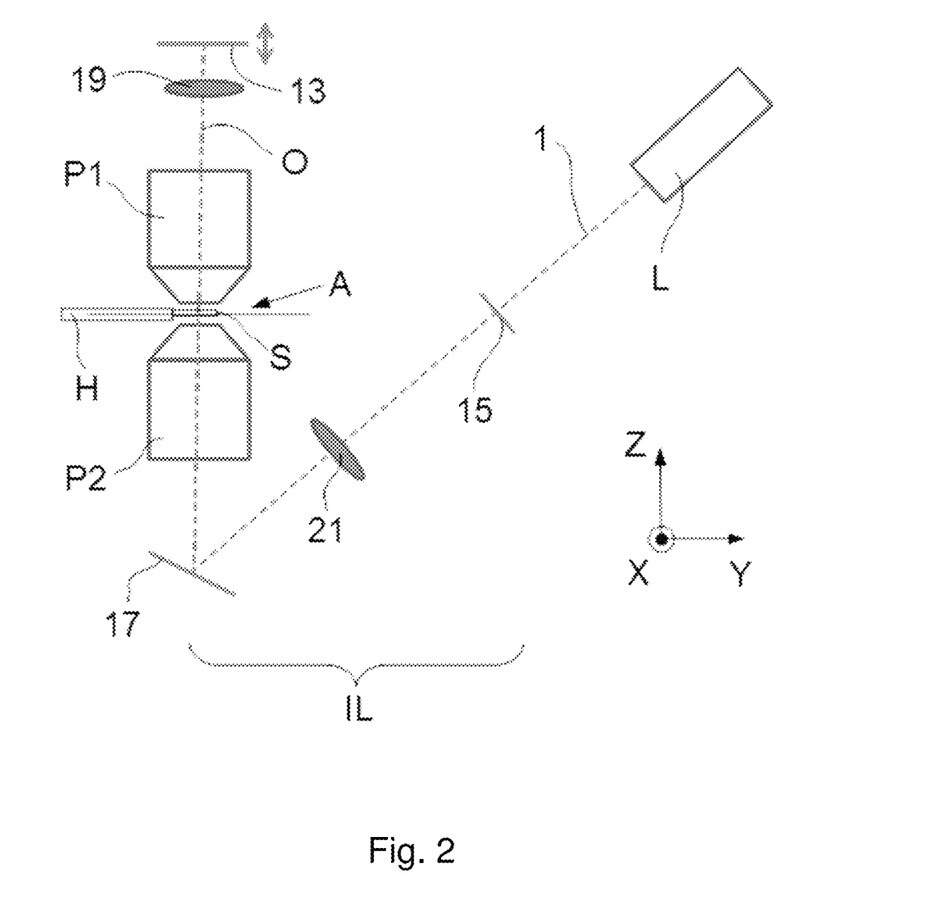
FIG. 2 illustrates a longitudinal cross-sectional view of part of another embodiment of a microscope according to the present invention.

In an alternative embodiment to that set forth in the previous paragraph, the illuminator comprises a laser located at a first side of said analysis location to direct an input beam along a common optical axis of said pair of projection systems and through said specimen in a first direction, a movable mirror, located at a second, opposite side of said analysis location and arranged normal to said common optical axis, to reflect said input beam back upon itself and through said specimen in a second, opposite direction. An example of such a set-up is depicted in FIG. 2. Such a configuration can be regarded as a "single-insertion" architecture, because the standing wave is generated using a single input beam, which, however, is reflected back upon itself by the employed movable mirror. In this case, a standing wave cavity is formed by said movable mirror and the lasing cavity in the laser. In general, the movable mirror will have associated collimation optics.

In a refinement of the set-up described in the previous paragraph, the illuminator can optionally comprise an optical diode or 50:50 plate beam splitter (for example) provided between said laser and said movable mirror. Such an embodiment serves to mitigate feedback effects in the lasing cavity.

Figure 3:
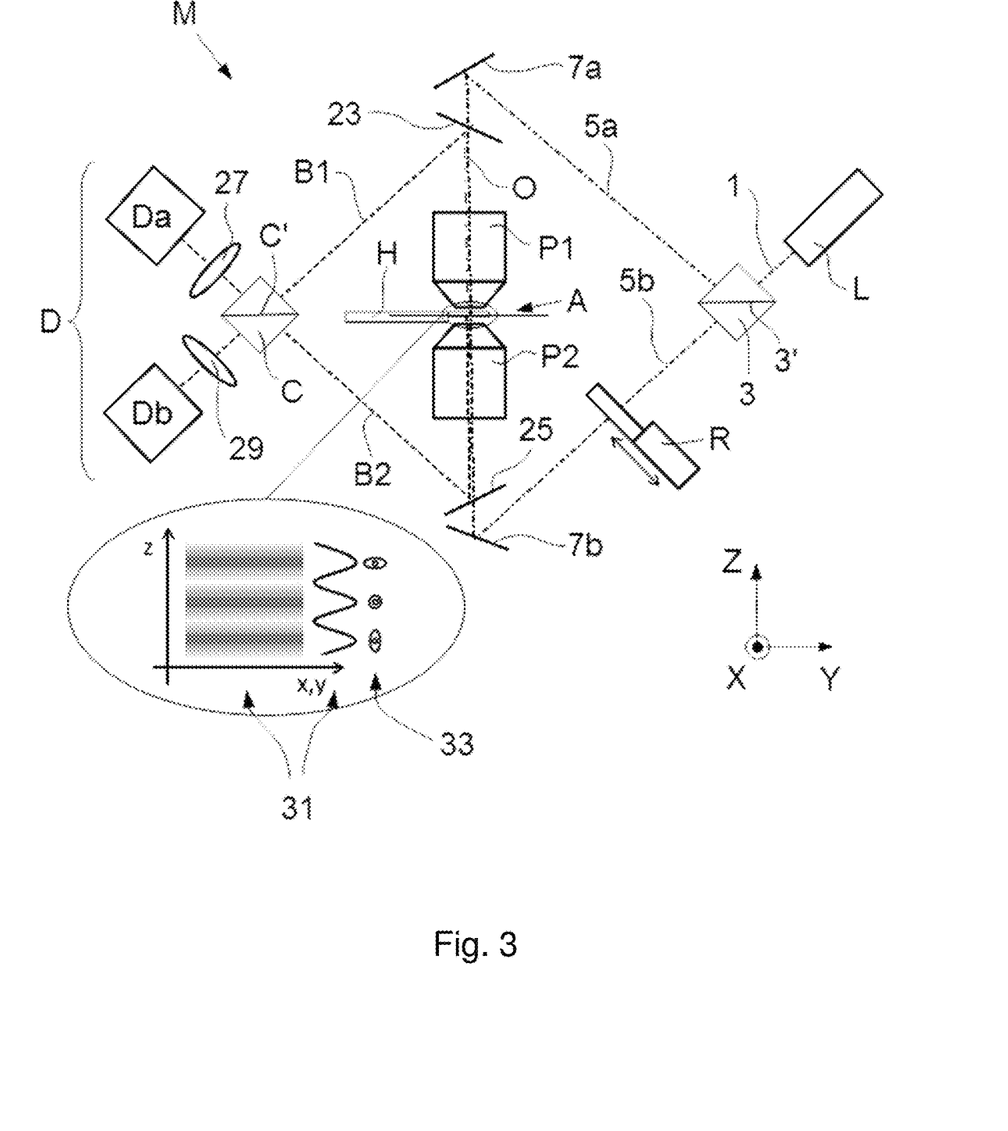
FIG. 3 illustrates a longitudinal cross-sectional view of a particular embodiment of a microscope according to the present invention.

In the single-insertion embodiments just discussed, adjusting the axial position of the movable mirror (along the local optical axis) allows the phase of the standing wave (at the analysis location) to be modified. A similar effect can be achieved in the preceding "dual-insertion" embodiment by, for example incorporating an adjustable optical retarder element in the path of at least one of the two input beams (as shown in FIGS. 1 and 3), and/or moving (at least) one of the pair of reflectors (and, if necessary, co-moving the beam splitter), so as to adjust the axial separation of the reflectors.

As already stated above, the standing wave utilized in the present invention may be generated using light from the activating light source (e.g. a laser with a wavelength of 405 nm) or the exciting light source (e.g. a laser with a wavelength of 488 nm, 561 nm, 639 nm or 750 nm). Such aspects relate to the illumination architecture of the inventive microscope. In addition to illumination optics, the invention is also concerned with the detection optics of the microscope. In that regard, an embodiment of the invention is characterized in that the employed optical combining element (OCE) comprises a two-way beam-splitter (as already alluded to above). This can be used in conjunction with a detector arrangement comprising two cameras, which look at two mutually phase-shifted outputs from the (OCE), see FIG. 3 for example. It will be disclosed herein why and how the standing wave generated in the present invention allows a less complicated OCE and a less complicated detector arrangement than in iPALM (and similar techniques).

As already set forth above, the present invention uses an innovative illumination set up, which correspondingly allows an innovative detection set-up to be employed. In a further aspect of the present invention, said standing wave is produced using said first type of radiation, and said selected fluorophores are activated in a depth region of the specimen proximal to a local maximum of said standing wave. Such a scenario exploits the fact that a standing wave generated in the illuminator according to the invention will intrinsically have localized maxima and minima extending axially through the specimen, and that this effect can be exploited to activate fluorophores in a depth region that is relatively thin relative to a period of the standing wave.

In a particular aspect of the invention, a wavefront modifying means may be used to produce astigmatism in light entering the optical combining element. To this end, one could, for example, employ a cylindrical lens or mirror, or introduce a (cylindrical) stress into a planar mirror (such as a folding mirror), in at least one or both of the dual detection branches of the microscope. Introducing astigmatism (more generally: wavefront modification that varies in polarity as a function of axial position) in this manner causes an associated Point Spread Function (PSF) to demonstrate ellipticity "oscillations" as a function of Z—changing from elongate along Y, to circular, to elongate along X, etc. Observing the form of this PSF at a given axial position can then be used to help determine a Z-value for that position—more specifically, it acts as a check on the "sign" of a Z-coordinate of known amplitude.

FIG. 1 illustrates a longitudinal cross-sectional view of part of an embodiment of a microscope (M) according to the present invention. More particularly, it illustrates an embodiment of an illuminator IL for such a microscope. In the Figure, a laser L produces a beam 1 of "input radiation", which, in the context of the present invention, may be an activation beam or an excitation beam for respectively activating/exciting a fluorophore in fluorescence microscopy. This beam 1 serves to illuminate (activate and/or excite) (a collection of fluorophores in) specimen S that is held on a specimen holder H at an analysis location A, (ultimately) causing (part of) specimen S to emit fluorescence light. The analysis location A is straddled by a pair of oppositely-located projection systems P1, P2, which will serve to collect this fluorescence light and direct it onto a detector arrangement D (to be discussed in the context of FIG. 3); for now, the present discussion will concentrate on the structure/functioning of illuminator IL.

The beam 1 encounters a two-way beam splitter 3, which divides the beam 1 into a pair of coherent light beams 5a, 5b, respectively located in two different "branches" or "arms" that originate from a beam-splitting surface 3' in item 3. The beams 5a, 5b subsequently impinge on a respective pair of reflectors (e.g. mirrors) 7a, 7b, which divert the beams 5a, 5b onto (or approximately onto) a common optical axis O of co-linear projection systems P1, P2; in this way, diverted beam 5a traverses analysis area A along O through P1, whereas diverted beam 5b traverses analysis area A along O through P2, and these two diverted beams produce a (longitudinal/axial) standing wave at location A (and elsewhere in the path/optical cavity A, 7a, 3, 7b, A). As schematically illustrated in FIG. 3, such a standing wave 31 will have alternating maxima and minima disposed along axis Z (of illustrated Cartesian coordinate system X, Y, Z), which extends parallel to 0.

Also symbolically/generically shown are optics 9, 11, which, for example, serve to focus/collimate the beams 5a, 5b. Moreover, as here depicted, an adjustable retarding element R is located in one of abovementioned "branches", thus allowing the phase of the generated standing wave 31 to be adjusted. As an alternative or supplement to this, one could also shift (at least) one of the reflectors 7a, 7b—e.g. shift reflector 7a as shown by the arrow symbol beside it.

FIG. 2 illustrates a longitudinal cross-sectional view of part of another embodiment of a microscope according to the present invention; more particularly, it illustrates an embodiment of an illuminator IL for such a microscope. Certain parts of FIG. 2 that are also present in FIG. 1 will not necessarily be discussed here; instead, the following discussion will concentrate on the differences between the two Figures.

In FIG. 2, a canted mirror 17 (optional) is located at a first side ("P2-side" or "upstream") of analysis location A; this is used to direct an input beam from a laser L along common optical axis O of projection systems P2, P1 and through specimen S in a first direction (+Z). Use is also made of a movable mirror (reflector) 13, which is arranged to be substantially normal to optical axis 0, can be displaced along O in a controlled manner, and is situated at a second, opposite side ("P1-side" or "downstream") of analysis location A; this serves to reflect said input beam back upon itself and through specimen S in a second, opposite direction (−Z). The outgoing (+Z) and returning (−Z) beam from L interact to produce a standing wave (inter alia at A). Displacement of mirror 13 along axis O allows the phase of this standing wave to be adjusted. Also symbolically/generically shown are optics 19, 21, which, for example, serve a focusing/collimation function.

Optionally present in FIG. 2 is a device 15 such as an optical diode 15 (e.g., a Faraday Isolator) or a 50:50 plate beam splitter.

FIG. 3 illustrates a longitudinal cross-sectional view of a particular embodiment of a microscope M according to the present invention. The illustrated microscope M comprises (inter alia) an illumination portion (to the right of axis 0) and a detection portion (to the left of axis 0). Said illumination portion essentially corresponds to the set-up shown in FIG. 1 (but could just as easily be based on the set-up shown in FIG. 2); therefore, so as to avoid unnecessary repetition, the following discussion will concentrate on said detection portion.

As already set forth above, illumination of (a collection of fluorophores in) specimen S—using suitably chosen activation and excitation wavelengths—will cause (certain of) those fluorophores to emit fluorescence light, which is (partially) collected by projection systems P1, P2. Using canted dichroic mirrors (reflectors) 23, 25 (positioned on axis 0), light collected by P1 and P2 is respectively directed as beams B1, B2 into (a respective pair of input faces of) Optical Combining Element (OCE) C—which, in the current invention, can be a (relatively simple) two-phase beam splitter (combiner) rather than a (more complicated) three-phase beam splitter (combiner); within OCE C, the beams B1 and B2 optically interfere and produce an interference pattern (not depicted). A detector arrangement D—which here comprises two detectors Da, Db—is used to examine this interference pattern, by simultaneously looking at it along two different (mutually phase-shifted) "channels": see FIG. 4A, for example. Also symbolically shown in FIG. 3 are generic optics 27, 29, which, for example, serve a focusing/collimation function. Ideally, the beam-splitting surface C' of OCE C is located in the same plane as specimen S; in that case, the phases of fluorescence emission of the beams B1 and B2 are "balanced" relative to the beam splitter position.

Figure 4A:
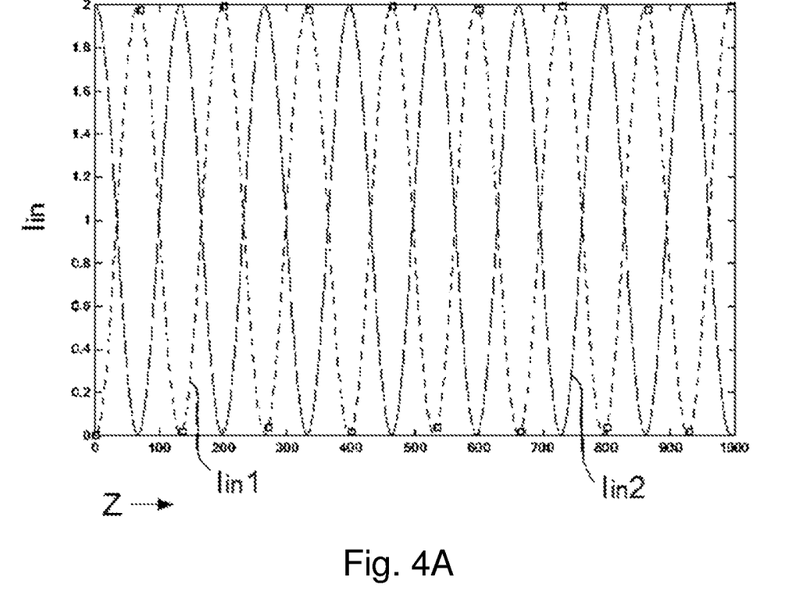
FIGS. 4A and 4B respectively show graphs of intensity (Iin) and Normalized Differential Intensity (Qin) as a function of axial position (Z) for two interfering light beams in an optical combining element.

Referring now to FIG. 4A, this shows a graph of measured intensity (Iin) versus axial position (Z) of (a fluorescing portion of) a specimen S as measured by detectors (cameras) Da (which registers intensity Iin1) and Db (which registers intensity Iin2) in a set-up such as that shown in FIG. 3 (whereby the suffix "in" denotes "interference"). It is noted that Iin1 and Iin2 demonstrate a sinusoidal dependence on Z. The intensity Iin on a given detector is determined by the sum/difference of the electromagnetic fields $E_{B1}$ and $E_{B2}$ associated with (travelling along) beams B1 and B2, respectively, whereby:

$$Iin1=(E_{B1}+E_{B2})^2 \; Iin2=(E_{B1}-E_{B2})^2.$$

The emission beam path of the cavity produces a phase shift of π between Iin1 and Iin2. The fluorescence wavelength in this particular instance is 530 nm, and the associated period of the intensity signals Iin1(Z) and Iin2(Z) is thus 530 nm/4=132.5 nm; however, these particular values are not limiting upon the current discussion. In a corresponding fashion, FIG. 4B shows the so-called Normalized Differential Intensity (Qin) as a function of Z, whereby:

$$Qin = (Iin1-Iin2)/(Iin1+Iin2).$$

Figure 4B:
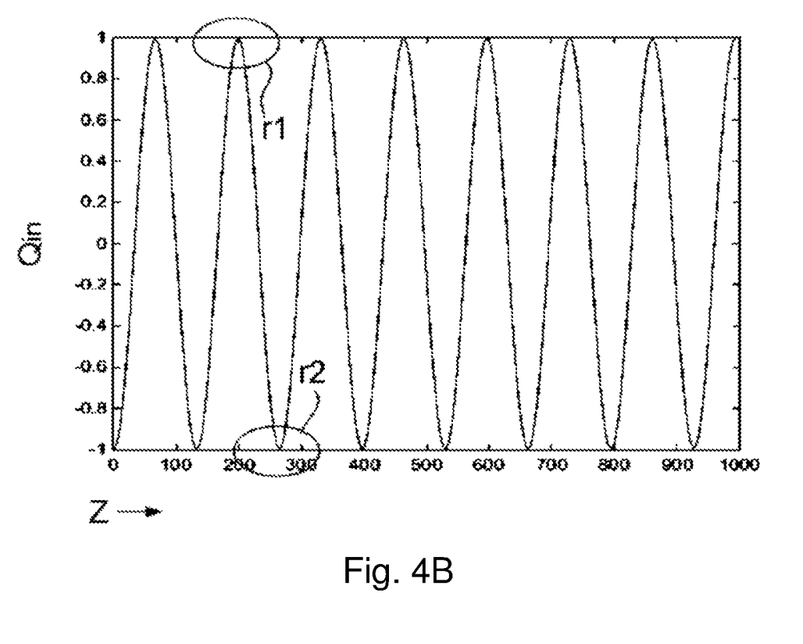

FIG. 4B is also sometimes referred to as a "calibration curve" for the employed detector arrangement. It is noted that the slope of this calibration curve reduces significantly in zones such as r1 and r2, which respectively correspond to a local maximum and local minimum of the curve; in these "dud" zones r1, r2, there is therefore a correspondingly lowered detection sensitivity. As a result, if, at/near a given Z-value, the value of Qin is extremal or near to extremal (corresponding to zones such as r1, r2), then it will be difficult to accurately determine the Z-value in question, which is an undesirable situation. This issue can be dealt with in different ways:

(a) In conventional iPALM, the underlying problem is addressed by using three detection channels, which are mutually phase-shifted by 120°/240°; as a result, if the Normalized Differential Intensity (NDI) for a given Z-value and a given pair of channels lands in a dud zone, then one can instead use the NDI based on a different pair of channels, which (for the same Z-value) will (necessarily) lie outside a dud zone.

Figure 5A:
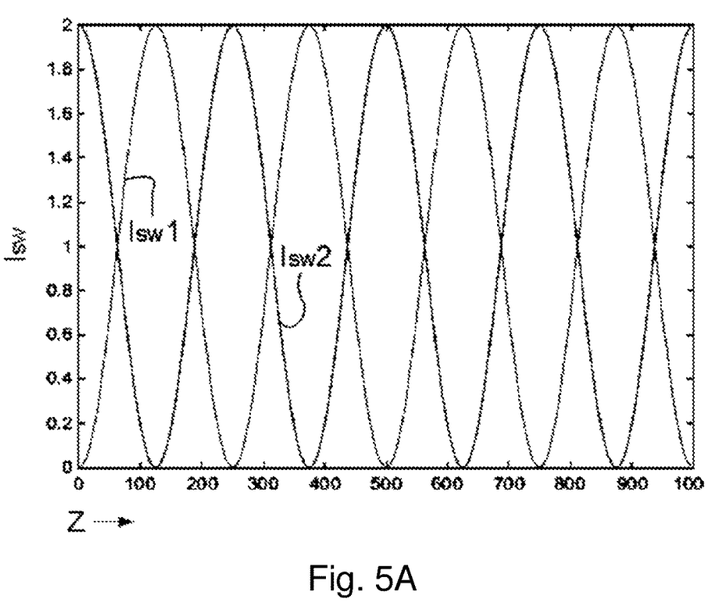
FIGS. 5A and 5B respectively show graphs of intensity (Isw) and Normalized Differential Intensity (Qsw) as a function of axial position (Z) for two phase-shifted standing waves, produced in an illuminator according to the current invention.
Figure 5B:
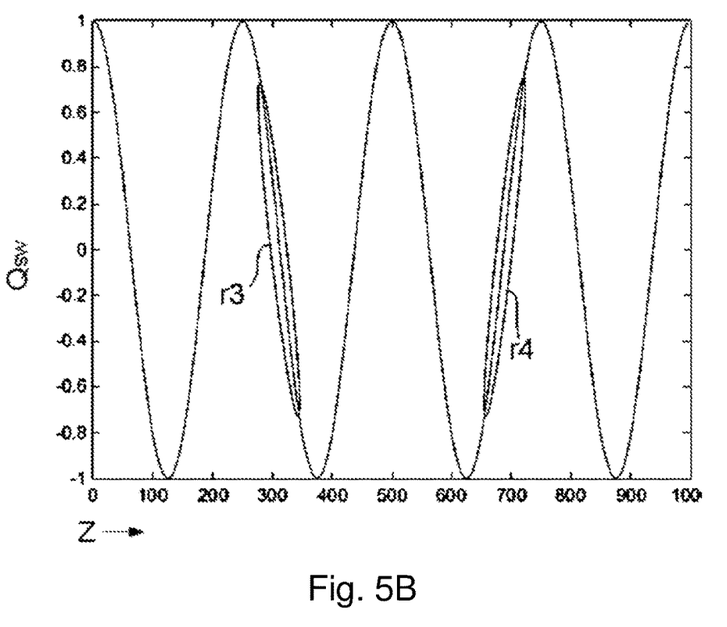

(b) In contrast, the present invention does not need to rely on such a third channel, and instead solves the problem of dud zones in a completely different manner. In this regard, reference is made to FIGS. 5A and 5B, which relate to the standing wave set-up of the current invention (whereby the suffix "sw" denotes "standing wave"). In this particular instance, the standing wave in question is generated using an illumination wavelength of 488 nm, but that is not limiting upon the current discussion. FIG. 5A shows the intensity (Isw1) of a first standing wave as a function of axial position (Z), and also shows the intensity (Isw2) of a second, axially displaced standing wave as a function of axial position (Z), whereby there is a phase difference $\Delta\varphi=\pi$ between said first and second standing waves. FIG. 5B shows the calibration curve corresponding to FIG. 5A [Qsw versus Z, with Qsw=(Isw1−Isw2)/(Isw1+Isw2)]. Note the "flank" zones r3, r4 in which the slope of the curve is greatest, corresponding to greatest sensitivity. By adding a phase shift $\delta$ to Isw1/Isw2 (e.g. by suitably moving retarding element R in FIG. 1 or 3), one can cause the calibration curve of FIG. 5B—and, therefore, the position of flank zones r3, r4—to shift along Z. In particular, one can Z-shift the calibration curve of FIG. 5B so that one of its flank zones (r3, r4; maximum sensitivity) corresponds to a dud zone (r1, r2; minimum sensitivity) of the calibration curve of FIG. 4B. In essence, one effectively takes four measurements, namely:

Iin1, Iin2 at a first standing wave phase value $\Delta\varphi$;

Iin1', Iin2' at a second standing wave phase value $\delta+\Delta\varphi$, whereby the Quantum Efficiency (emission brightness) of the observed fluorescing fluorophore(s) should not (significantly) change during the measurement process (so that an observed intensity change can be validly attributed to a standing wave phase shift rather than a change in intrinsic brightness of the fluorophore(s)); this will typically imply an exposure time of the order of about 1-100 ms, for example. From these measurements, the Z-position of an observed portion (fluorescing fluorophore(s)) of the specimen can be determined. This can be done by "fitting" the measured intensity values to reference Q-versus-Z graphs obtained in a (previously performed) calibration session in which intensity signals from a test specimen (such as a gold nanoparticle) are registered as the test specimen is deliberately moved along Z.

With reference to the elucidation already given above regarding FIGS. 4A, 4B, 5A and 5B, a supplemental description will now be given as to how an inventive microscope such as that depicted in FIG. 3 can be used. More particularly, the following discussion will concentrate on certain aspects of detection signal analysis/processing/interpretation.

Figure 6:
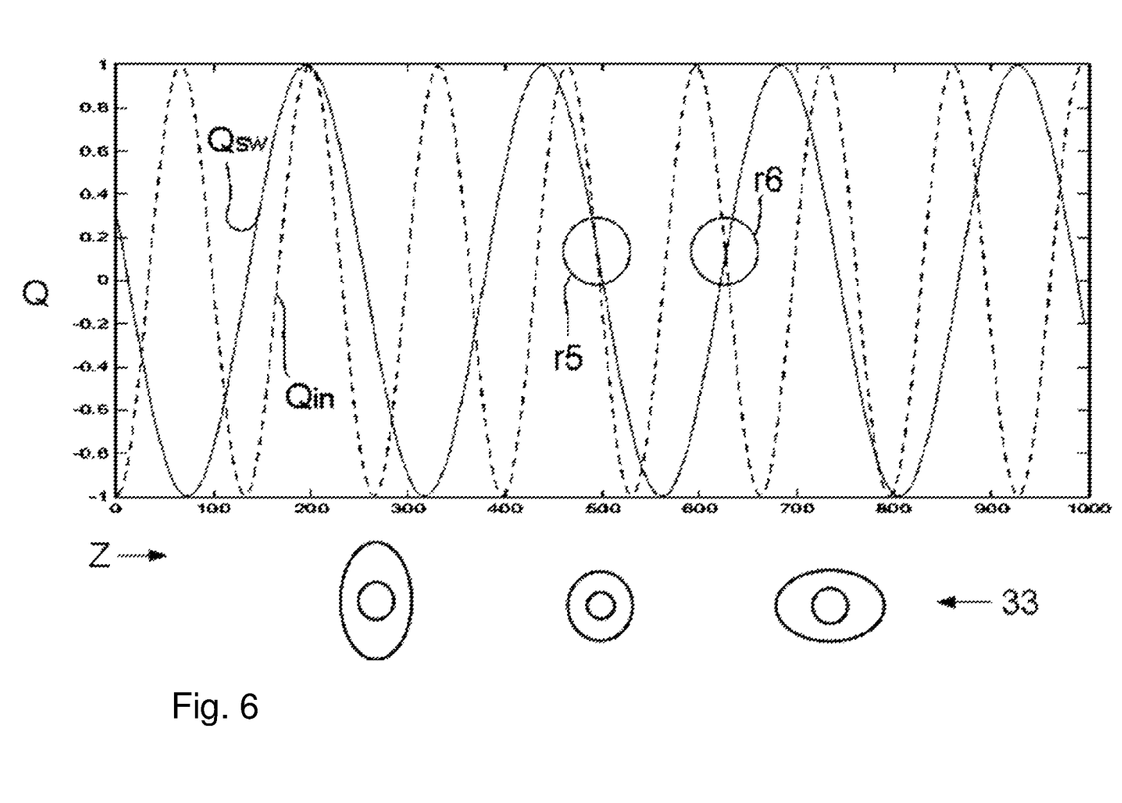
FIG. 6 illustrates a graph in which curves such as those in FIGS. 4B and 5B have been combined/superimposed.

FIG. 6 illustrates a graph in which curves such as those in FIGS. 4B and 5B have been combined/superimposed. Because the component curves have different frequencies (as a function of Z), they will inevitably cross each other at certain points—such as in depicted zones r5, r6, for example. In such zones, measurement sensitivity will tend to be relatively low.

This problem can be addressed using a technique that is also exploited in iPALM. If the wavefront of the fluorescence light reaching the OCE C is deliberately deformed so as to introduce astigmatism—e.g. by deliberately mechanically stressing one/preferably both of the folding mirrors 23, 25 in FIG. 3—then the associated Point Spread Function (PSF) 33 will demonstrate ellipticity "oscillations" as a function of Z—changing from elongate along Y, to circular, to elongate along X, etc. Observing the form of the PSF 33 at a given position can then be used to deduce a Z-value for that position. This is schematically depicted in FIG. 6, by illustrating exemplary PSF forms as a function of Z along the abscissa axis.

The basic mathematical analysis of the interference pattern in a microscope according to the current invention is similar to that pertaining to iPALM. For more information in this regard, reference is (for example) made to the mathematical discussion in U.S. Pat. No. 7,924,432, which is incorporated herein by reference for all purposes.

What is claimed is:

1. An apparatus comprising:
   an illuminator, for illuminating a specimen with a standing wave of input radiation at an analysis location to cause the specimen to fluoresce, the specimen arranged in the analysis location;
   a pair of projection systems, arranged at opposite sides of the analysis location, coupled to collect at least a portion of the fluorescence and direct a corresponding pair of fluorescence light beams into a respective pair of inputs of an optical combining element;
   a wavefront modifier for producing astigmatism in at least one of the fluorescence light beams entering the optical combining element; and
   a detector for examining output light from said combining element.

2. The apparatus of claim 1, wherein the wavefront modifier is a cylindrical lens.

3. The apparatus of claim 1, wherein the wavefront modifier is planar mirror having a cylindrical stress induced thereon.

4. The apparatus of claim 3, wherein the planar mirror is a folding mirror.

5. The apparatus of claim 1, wherein the wavefront modifier is arranged to produce astigmatism in both fluorescence light beams prior to entering the optical combining element.

6. The apparatus of claim 1, wherein the detector includes two interferometric detection branches.

7. The apparatus of claim 1, wherein the illuminator comprises:
   a beam splitter, to produce a pair of coherent beams from a single source; and
   a pair of reflectors to direct each of said pair of coherent beams through a respective one of said pair of projection systems.

8. The apparatus of claim 7, wherein the illuminator comprises an adjustable optical retarding element arranged in a path of at least one of the coherent beams.

9. The apparatus of claim 1, wherein the illuminator comprises:
   a laser, located at a first side of the analysis location, to direct an input beam along a common optical axis of the pair of projection systems and through the specimen in a first direction; and
   a movable mirror, located at a second, opposite side of the analysis location and arranged normal to the common optical axis, to reflect the input beam back upon itself and through the specimen in a second, opposite direction.

10. The apparatus of claim 1, wherein the optical combining element comprises a two-way beam-splitter.

11. The apparatus of claim 1, wherein the input radiation comprises:

a first type of radiation, for activating selected fluorophores in the specimen; and a second type of radiation, for exciting a set of activated fluorophores, with the resultant emission of fluorescence light, wherein the standing wave is produced using either the first or second type of radiation.

12. The apparatus of claim 11, wherein:

the standing wave is produced using the first type of radiation; and the selected fluorophores are activated in a depth region of the specimen proximal to a local maximum of the standing wave.

13. A method comprising:

producing a standing wave of input radiation at an analysis location;

in response to the standing wave of input radiation, causing at least one fluorophore to fluoresce, the fluorophore arranged in the analysis location;

collecting the fluorescence by a pair of projection systems arranged on opposing sides of the analysis location;

directing, by the pair of projection systems, a corresponding pair of fluorescence light beams toward an optical combiner;

introducing astigmatism in the corresponding pair of fluorescence light beams;

optically combining, by the optical combiner, the corresponding pair of fluorescence light beams to form an interference pattern;

recording a first intensity distribution of said interference pattern;

altering a phase of said standing wave; and deriving an axial position of said fluorophore relative to a common optical axis of said pair of projection systems based on the intensity of the interference pattern.

14. The method of claim 13, wherein introducing astigmatism in the corresponding pair of fluorescence light beams includes passing the corresponding pair of fluorescence light beams through respective cylindrical lenses.

15. The method of claim 13, wherein introducing astigmatism in the corresponding pair of fluorescence light beams includes passing the corresponding pair of fluorescence light beams through respective planar mirrors having a cylindrical stress induced thereon.

16. The method of claim 13, wherein altering a phase of the standing wave includes inserting an optical retarder into a path of the input radiation.

17. The method of claim 13, wherein altering a phase of the standing wave includes adjusting a path length of the input radiation.

18. The method of claim 13, wherein the optical combiner is a two-way beam splitter.

19. The method of claim 13, wherein producing a standing wave of input radiation at an analysis location includes directing a laser into the analysis location from opposing sides of the analysis location.

20. The method of claim 13, wherein producing a standing wave of input radiation at an analysis location includes directing a laser into the analysis location from a first side of the analysis location.

* * * * *